(12) United States Patent
Mallo et al.

(10) Patent No.: US 8,512,684 B2
(45) Date of Patent: Aug. 20, 2013

(54) PROCESS FOR THE PREPARATION OF INVERSE LATEX OF ACRYLAMIDE-BASED POLYMERS AND COMPOSITION COMPRISING SAID LATEX

(75) Inventors: Paul Mallo, Croissy-sur-Seine (FR); Olivier Braun, Castres (FR); Francois Guy, Launaguet (FR); Audrey Bonnardel, Castres (FR)

(73) Assignees: Societe d'Exploitation de Produits pour les Industries Chimiques SEPPIC, Paris (FR); Scott Bader Company Limited, Wollaston, Wellingborough (GB)

( * ) Notice: Subject to any disclaimer, the term of this patent is extended or adjusted under 35 U.S.C. 154(b) by 156 days.

(21) Appl. No.: 12/738,150

(22) PCT Filed: Oct. 15, 2008

(86) PCT No.: PCT/EP2008/063876
§ 371 (c)(1), (2), (4) Date: Apr. 15, 2010

(87) PCT Pub. No.: WO2009/053287
PCT Pub. Date: Apr. 30, 2009

(65) Prior Publication Data
US 2010/0233108 A1 Sep. 16, 2010

(30) Foreign Application Priority Data
Oct. 25, 2007 (EP) .................................. 07301490

(51) Int. Cl.
*A61K 8/00* (2006.01)
*A61K 8/18* (2006.01)
*A61Q 17/04* (2006.01)

(52) U.S. Cl.
USPC .............. 424/59; 514/299; 514/557; 523/337

(58) Field of Classification Search
None
See application file for complete search history.

(56) References Cited

U.S. PATENT DOCUMENTS

| 5,804,202 | A * | 9/1998 | Chaudhry et al. ............ 424/401 |
| 7,033,600 | B1 | 4/2006 | Mallo et al. |
| 2006/0269490 | A1 * | 11/2006 | Braun et al. .................... 424/59 |
| 2007/0265386 | A1 | 11/2007 | Mallo et al. |

FOREIGN PATENT DOCUMENTS

| EP | 0 503 853 | 9/1992 |
| FR | 2 786 493 | 6/2000 |
| FR | 2 873 126 | 1/2006 |
| WO | 00/32639 | 6/2000 |
| WO | 01/35922 | 2/2001 |

OTHER PUBLICATIONS

International Search Report dated Feb. 2, 2009, from corresponding PCT application.

* cited by examiner

*Primary Examiner* — Fereydoun G Sajjadi
*Assistant Examiner* — David Browe
(74) *Attorney, Agent, or Firm* — Young & Thompson

(57) ABSTRACT

Process for the preparation of a composition including an oil phase, an aqueous phase, at least one emulsifying system of water-in-oil (W/O) type, optionally at least one emulsifying system of oil-in-water (O/W) type, in the form of an inverse latex including from 20% to 70% by weight and preferably from 25% to 50% by weight of a branched or crosslinked polyelectrolyte, characterized in that the polyelectrolyte is a copolymer of 2-acrylamido-2-methylpropanesulfonic acid partially or totally salified with acrylamide and optionally one or more monomers chosen from monomers containing a partially or totally salified weak acid function and/or from neutral monomers other than acrylamide, the production process being characterized in that the preparation of the aqueous phase includes the dissolution in the aqueous medium of solid 2-acrylamido-2-methyl propanesulfonic acid before neutralization. Cosmetic, dermopharmaceutical or pharmaceutical composition including the inverse latex directly obtained by the process.

10 Claims, No Drawings

PROCESS FOR THE PREPARATION OF INVERSE LATEX OF ACRYLAMIDE-BASED POLYMERS AND COMPOSITION COMPRISING SAID LATEX

The present patent application relates to a preparation process a water-in-oil inverse latex, and to the use of the said inverse latex as thickeners and/or emulsifiers for skincare and haircare products or for the manufacture of cosmetic, dermocosmetic, dermopharmaceutical or pharmaceutical preparations.

The thickeners used in the cosmetics or pharmaceutical industry, are intended to thicken aqueous phases, lotions or cream-gels. In the case of cream-gels, an emulsifier is also added, especially when it is desired to incorporate a high content of oil into the formulation. However, emulsifiers are often products with a low molecular weight, which are potentially less tolerated by the skin than polymers. Furthermore, the use of polymers allows the preparation of cream-gels without heating, which reduces the manufacturing costs while at the same time keeping the heat-sensitive molecules intact.

Accordingly, it has been sought to develop polymers that are both thickeners and emulsifiers. Among them, reference is made to self-invertible inverse latex of copolymer of 2-acrylamido-2-methyl propanesulfonic acid (AMPS) and acrylamide crosslinked with N,N-methylene bis(acrylamide), partially or totally neutralized in the form sodium or potassium salt, said polymeric inverse emulsion being disclosed in European patent application publication EP 0 503 853 and in International publication WO 01/35922.

In both documents, the preparation process involves the use of 50 to 60% weight by weight aqueous solution of AMPS sodium salt and acrylamide and the polymerization is made at a pH=7. Such an AMPS sodium salt solution is available as a 55% weight by weight solution at CIM chemicals under the trade name ATBSNa or as 50% or 58% weight by weight solution at Lubrizol under the trade names AMPS2405 and AMPS2405A. It is known that such commercial aqueous solutions contains until 100 ppm to 200 ppm of stabilizing agents, in order to prevent inter alia, the monomer polymerization during the storage of the composition. The same applies for acrylamide, which is commercially available as a 50% weight by weight acrylamide, such aqueous acrylamide solutions containing lower levels of copper derivatives stabilizing agents.

International publication WO 00/32639 discloses a process for the preparation of inversed latex of AMPS without using alcanolamide type surfactant. Example 1 of said patent application discloses a process wherein AMPS free acids, then a 50% weight/weight aqueous solution of acrylamide and auxiliary compounds are poured into an alkaline aqueous solution, which pH is afterwards adjusted to about 5 with water to form the aqueous phase, which is involved in the polymerization by emulsion.

Although the process for their production involves the use of acrylamide, the amount of such a reactant in the final composition, does not indeed, exceed 2 ppm, which is until now considered in most of the environmental regulations, as an acceptable quantity.

It has however been observed that, depending on the storage conditions and of the storage duration, the concentration of acrylamide in some samples of final composition had increased over the above-mentioned 2 ppm limit until becoming prejudicial to the use of said composition in topical formulations.

That is why, according to a first embodiment, the invention relates to an improved production process of inverse latex of acrylamide based polymers, which avoids acrylamide release in the final composition.

According to a more specific aspect, the invention relates to a process for the preparation of a composition comprising an oil phase, an aqueous phase, at least one emulsifying system of water-in-oil (W/O) type, optionally at least one emulsifying system of oil-in-water (O/W) type, in the form of an inverse latex comprising from 20% to 70% by weight and preferably from 25% to 50% by weight of a branched or crosslinked polyelectrolyte, wherein the said polyelectrolyte is a copolymer of 2-acrylamido-2-methylpropanesulfonic acid partially or totally salified with acrylamide and optionally one or more monomers chosen from monomers containing a partially or totally salified weak acid function and/or from neutral monomers other than acrylamide, said preparation process being an inversed emulsion polymerization process wherein the polymerization of the monomers is conducted in a water-in oil emulsion, characterized in that said process comprises:

A step a) wherein a powder of 2-methyl-2-[(1-oxo-2-propenyl)amino]-1-propanesulfonic in acid form is mixed with an aqueous solution of acrylamide and optionally a chelating agent and/or the crosslinking agent, to form an aqueous solution;

A step b) wherein said aqueous solution obtained at step a) is then progressively neutralized by an aqueous alkalinized solution, Optionally a step c) wherein the crosslinking agent is added to said neutralized aqueous solution obtained at step b), and A step d) wherein the pH of said neutralized solution obtained at step b) or at step c); is adjusted to about 6 with additional powder of 2-methyl-2-[(1-oxo-2-propenyl)amino]-1-propanesulfonic in acid form and water to form the aqueous phase, which is involved in the subsequent inversed emulsion polymerization.

In the composition as hereinabove defined, 2-methyl-2-[(1-oxo-2-propenyl)amino]-1-propanesulfonic acid is preferably partially or totally salified in the form of an alkali metal salt, for example the sodium salt or the potassium salt, the ammonium salt, an amino alcohol salt, for instance the monoethanolamine salt, or an amino acid salt, for instance the lysine salt.

The weak acid function of the monomers comprising one is especially a partially salified carboxylic acid function. The said monomers may be, for example, partially or totally salified acrylic acid, methacrylic acid, itaconic acid, maleic acid or 3-methyl-3-[(1-oxo-2-propenyl)amino]butanoic acid. They are preferably partially or totally salified in the form of an alkali metal salt, for instance the sodium salt or the potassium salt, the ammonium salt, an amino alcohol salt, for instance the monoethanolamine salt, or an amino acid salt, for instance the lysine salt.

The neutral monomers other than acrylamide are especially chosen from methacrylamide, diacetoneacrylamide, N-isopropylacrylamide, N-[2-hydroxy-1,1-bis[(hydroxymethyl)ethyl]]propenamide [or tris(hydroxymethyl)acrylamidomethane or N-tris(hydroxymethyl)methylacrylamide also known as THAM], 1e N,N-dimethylacrylamide, (2-hydroxyethyl)acrylate, (2,3-dihydroxypropyl)acrylate, (2-hydroxyethyl)methacrylate, (2,3-dihydroxypropyl)methacrylate, an ethoxylated derivative with a molecular weight of between 400 and 1000, of each of these esters, or vinylpyrrolidone.

The polyelectrolyte present in the composition as hereinabove defined comprises between 60 mol % and 20 mol % of partially or totally salified 2-methyl-2-[(1-oxo-2-propenyl)amino]-1-propanesulfonic acid monomer and between 40 mol % and 80 mol % of acrylamide monomer.

According to one particular aspect of the present invention, the polyelectrolyte present in the composition comprises between 50% and 30% of partially or totally salified 2-methyl-2-[(1-oxo-2-propenyl)amino]-1-propanesulfonic acid monomer and between 50 mol % and 70 mol % of acrylamide monomer.

When the polyelectrolyte present in the composition as hereinabove defined is a copolymer of partially or totally salified 2-acrylamido-2-methylpropanesulfonic acid, of acrylamide and of one or more monomers chosen from monomers containing a weak acid function and/or neutral monomers other than acrylamide, the mole proportion of all of the monomers chosen from the monomers containing a weak acid function and the neutral monomers other than acrylamide is greater than 0% and less than or equal to 30%. In this case said one or more monomer is added in step a) of the hereinabove defined process.

In the first case, the mole ratio between the acrylamide and all of the monomers chosen from the monomers containing a weak acid function and the neutral monomers other than acrylamide is preferably greater than or equal to 1.

The term "branched polymer" denotes a non-linear polymer containing side chains so as to obtain, when this polymer is dissolved in water, extensive entanglement leading to very high viscosities at low shear.

The term "crosslinked polymer" denotes a non-linear polymer in the form of a water-insoluble but water-swellable three-dimensional network thus leading to the production of a chemical gel.

The composition according to the invention may comprise crosslinked units and/or branched units.

When the polymer present in the composition that is the subject of the present invention is crosslinked, it is more particularly crosslinked with a diethylenic or polyethylenic compound in a mole proportion, expressed relative to the monomers used, of from 0.005% to 1%, more particularly from 0.010% to 0.20% and still more particularly from 0.015% to 0.15%. Preferably, the crosslinking agent and/or the branching agent is chosen from ethylene glycol dimethacrylate, diethylene glycol diacrylate, sodium diallyloxyacetate, ethylene glycol diacrylate, diallylurea, triallylamine, trimethylolpropane triacrylate and methylenebis (acrylamide).

In the composition as hereinabove defined, the emulsifying system of water-in-oil (W/O) type consists either of a sole surfactant or of a mixture of surfactants on condition that the HLB value of the said mixture is low enough to induce water-in-oil emulsions. As emulsifiers of water-in-oil type, there are, for example, sorbitan esters, for instance sorbitan oleate, for instance the product sold by the company SEPPIC under the name Montane™ 80, sorbitan isostearate, for instance the product sold by the company SEPPIC under the name Montane™ 70, or sorbitan sesquioleate, for instance the product sold by the company SEPPIC under the name Montane™ 83. There are also certain polyethoxylated sorbitan esters, for example pentaethoxylated sorbitan monooleate, for instance the product sold by the company SEPPIC under the name Montanox™ 81 or pentaethoxylated sorbitan isostearate, for instance the product sold under the name Montanox™ 71 by the company SEPPIC. There is also diethoxylated oleo-cetyl alcohol, for instance the product sold under the name Simulsol™ OC 72 by the company SEPPIC, tetraethoxylated lauryl acrylate, for instance the product sold under the name Blemmer™ ALE 200 or polyesters with a molecular weight of between 1000 and 3000, produced from condensation between a poly(isobutenyl)succinic acid or its anhydride and polyethylene glycol, such as Hypermer™ 2296 sold by the company Uniqema, or, finally, block copolymers with a molecular weight of between 2500 and 3500, for instance Hypermer™ B246 sold by the company Uniqema or Simaline™ IE 200 sold by the company SEPPIC.

The composition that is the subject of the present invention generally comprises from 2% to 8% by weight of emulsifying system of water-in-oil (W/O) type.

When the composition as hereinabove defined comprises an emulsifying system of oil-in-water (O/W) type, it consists either of a sole surfactant or of a mixture of surfactants, on condition that the HLB value of the said mixture is high enough to induce oil-in-water emulsions. As emulsifiers of oil-in-water type, there are, for example, ethoxylated sorbitan esters, for instance sorbitan oleate polyethoxylated with 20 mol of ethylene oxide, sold by the company SEPPIC under the name Montanox™ 80, sorbitan laurate polyethoxylated with 20 mol of ethylene oxide, sold by the company SEPPIC under the name Montanox™ 20, castor oil polyethoxylated with 40 mol of ethylene oxide, sold under the name Simulsol™ OL50, decaethoxylated oleodecyl alcohol, sold by the company SEPPIC under the name Simulsol™ 00710, heptaethoxylated lauryl alcohol, sold under the name Simulsol™ P7 or sorbitan monostearate polyethoxylated with 20 mol of ethylene oxide, sold by the company SEPPIC under the name Montanox™ 60.

When the composition that is the subject of the present invention comprises an emulsifying system of oil-in-water (O/W) type, it generally comprises from 3% to 8% by weight of this system.

According to one particular aspect of the present invention, the composition as hereinabove defined comprises an (O/W) emulsifying system.

In the composition that is the subject of the present invention, the oil phase comprises a commercial mineral oil containing saturated hydrocarbons, for instance paraffins, isoparaffins or cycloparaffins, having at room temperature a density of between 0.7 and 0.9 and a boiling point of greater than about 250° C., for instance Marcol™ 52, Isopar™ M or Isopar™ L sold by Exxon Chemical; isohexadecane, identified in Chemical Abstracts by the number RN=93685-80-4, which is a mixture of $C_{12}$, $C_{16}$ and $C_{20}$ isoparaffins containing at least 97% of $C_{16}$ isoparaffins, among which the main constituent is 2,2,4,4,6,8,8-heptamethylnonane (RN=4390-04-9); it is sold in France by the company Bayer, or isododecane also sold in France by the company Bayer; or a synthetic oil such as hydrogenated polydecene or hydrogenated polyisobutene, sold in France by the company Ets B. Rossow et Cie under the name Parleam-Polysynlane™. It is cited in: Michel and Irene Ash; Thesaurus of Chemical Products, Chemical Publishing Co. Inc. 1986 Volume I, page 211 (ISBN 0 7131 3603 0); or a plant oil, for instance squalane of plant origin sold in France by the company Sophim, under the name Phytosqualane™ and identified in Chemical Abstracts by the number RN=111-01-3; it is a mixture of hydrocarbons containing more than 80% by weight of 2,6,10,15,19,23-hexamethyltetracosane, or of a mixture of several of these oils.

The oil phase may also comprise fatty acid esters.

In the context of the present invention, the term "fatty acid ester" means a compound of formula (I):

$$R_1—(C=O)—O—[[CH_2—CH[O—[C(=O)]_mR_2]—CH_2—O]_n—[C(=O)]_p]_q—R_3 \quad (I)$$

In which:

$R_1$ represents a saturated or unsaturated, linear or branched hydrocarbon-based chain containing from 7 to 30 carbon atoms, $R_2$ represents, independently of $R_1$, a hydrogen atom or a saturated or unsaturated, linear or branched hydrocarbon-based chain containing from 7 to 30 carbon atoms, $R_3$ represents, independently of $R_1$ or $R_2$, a hydrogen atom or a saturated or unsaturated, linear or branched hydrocarbon-based chain containing from 1 to 30 carbon atoms, m, n, p and q are, independently of each other, equal to 0 or 1, it being understood that when $R_3$ represents a hydrogen atom, q is other than 0.

In the formula (I) as hereinabove defined, $R_1$, $R_2$ and $R_3$ especially represent, independently of each other, a radical chosen from heptyl, octyl, nonyl, decyl, undecyl, dodecyl, tridecyl, tetradecyl, pentadecyl, hexadecyl, heptadecyl, octadecyl, nonadecyl, eicosyl, uneicosyl, docosyl, heptadecenyl, eicosenyl, uneicosenyl, docosenyl, heptade-cadienyl and decenyl radicals; the group $R_1$—C(=O)— more particularly represents one of the following radicals: octanoyl (caprylyl), decanoyl, undecylenoyl, dodecanoyl (lauroyl), tetradecanoyl (myristyl), hexadecanoyl (palmitoyl), octadecanoyl (stearyl), eicosanoyl (arachidoyl), docosanoyl (behenoyl), 8-octadecenoyl (oleyl), eicosenoyl (gadoloyl), 13-docosenoyl (erucyl), 9,12-octadecadienoyl (linoleoyl), 9,12,15-octadecatrienoyl (linolenoyl).

The oil phase may more particularly comprise a compound of formula (Ia):

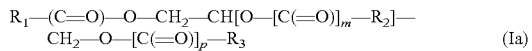

$$R_1\text{—}(C{=}O)\text{—}O\text{—}CH_2\text{—}CH[O\text{—}[C({=}O)]_m\text{—}R_2]\text{—}CH_2\text{—}O\text{—}[C({=}O)]_p\text{—}R_3 \quad (Ia)$$

Corresponding to formula (I) as hereinabove defined in which q and n are equal to 1, or a mixture of compounds of formula (Ia). In this case, it is preferably Either a compound of formula $(Ia_1)$:

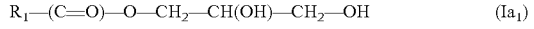

$$R_1\text{—}(C{=}O)\text{—}O\text{—}CH_2\text{—}CH(OH)\text{—}CH_2\text{—}OH \quad (Ia_1)$$

Corresponding to formula (Ia) as hereinabove defined in which m and p are equal to 0 and $R_2$ and $R_3$ represent a hydrogen atom, Or a compound of formula $(Ia_2)$:

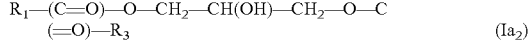

$$R_1\text{—}(C{=}O)\text{—}O\text{—}CH_2\text{—}CH(OH)\text{—}CH_2\text{—}O\text{—}C({=}O)\text{—}R_3 \quad (Ia_2)$$

Corresponding to formula (Ia) as hereinabove defined in which p is equal to 1, m is equal to 0 and $R_2$ represents a hydrogen atom, Or a compound of formula $(Ia_3)$:

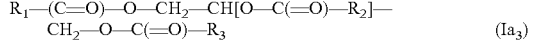

$$R_1\text{—}(C{=}O)\text{—}O\text{—}CH_2\text{—}CH[O\text{—}C({=}O)\text{—}R_2]\text{—}CH_2\text{—}O\text{—}C({=}O)\text{—}R_3 \quad (Ia_3)$$

corresponding to formula (Ia) as hereinabove defined in which m and p are equal to 1, Or a mixture of compounds of formulae $(Ia_1)$, $(Ia_2)$ and/or $(Ia_3)$.

As examples of compounds of formula $(Ia_1)$, $(Ia_2)$ or $(Ia_3)$, there are, for example, fatty acid triglycerides or fatty acid mixtures such as the mixture of fatty acid triglycerides containing from 6 to 10 carbon atoms, sold under the name Softenol™ 3819, the mixture of fatty acid triglycerides containing from 8 to 10 carbon atoms, sold under the name Softenol™ 3108, the mixture of fatty acid triglycerides containing from 8 to 18 carbon atoms, sold under the name Softenol™ 3178, the mixture of fatty acid triglycerides containing from 12 to 18 carbon atoms, sold under the name Softenol™ 3100, the mixture of fatty acid triglycerides containing 7 carbon atoms, sold under the name Softenol™ 3107, the mixture of fatty acid triglycerides containing 14 carbon atoms, sold under the name Softenol™ 3114, or the mixture of fatty acid triglycerides containing 18 carbon atoms, sold under the name Softenol™ 3118, glyceryl dilaurate, glyceryl dioleate, glyceryl isostearate, glyceryl distearate, glyceryl monolaurate, glyceryl monooleate, glyceryl monoisostearate or glyceryl monostearate, or a mixture of these compounds.

The oil phase may more particularly comprise a compound of formula (Ib):

$$R_1\text{—}(C{=}O)\text{—}O\text{—}R_3 \quad (Ib)$$

Corresponding to formula (I) as hereinabove defined in which q is equal to 0, or a mixture of compounds of formula (Ib).

An example of a compound of formula (Ib) is, for example, octyl palmitate.

The inverse latex as hereinabove defined generally contains from 4% to 10% by weight of emulsifiers.

Its oil phase represents from 15% to 40% and preferably from 20% to 25% of the total weight of the composition.

The aqueous phase represents from 2% to 40% of the total weight of the composition.

According to another particular aspect of the present invention, a subject thereof is a composition obtained by the process, as hereinabove defined in which the copolymer is chosen from:

Crosslinked copolymers of 2-methyl-2-[(1-oxo-2-propenyl)amino]-1-propanesulfonic acid partially salified in the form of the sodium salt and of acrylamide;

Crosslinked copolymers of 2-methyl-2-[(1-oxo-2-propenyl)amino]-1-propanesulfonic acid partially salified in the form of the ammonium salt and of acrylamide;

Crosslinked copolymers of 2-methyl-2-[(1-oxo-2-propenyl)amino]-1-propanesulfonic acid partially salified in the form of the potassium salt and of acrylamide;

crosslinked terpolymers of 2-methyl-2-[(1-oxo-2-propenyl)amino]-1-propanesulfonic acid partially salified in the form of the sodium salt, of the potassium salt or of the ammonium salt, of acrylic acid partially salified in the form of the sodium salt, the potassium salt or the ammonium salt and of acrylamide;

crosslinked tetrapolymers of 2-methyl-2-[(1-oxo-2-propenyl)amino]-1-propanesulfonic acid partially salified in the form of the sodium salt, the potassium salt or the ammonium salt, of acrylic acid partially salified in the form of the sodium salt, the potassium salt or the ammonium salt, of N,N-dimethylacrylamide and of acrylamide;

Crosslinked terpolymers of 2-methyl-2-[(1-oxo-2-propenyl)amino]-1-propanesulfonic acid partially salified in the form of the sodium salt, the potassium salt or the ammonium salt, of N,N-dimethylacrylamide and of acrylamide;

Crosslinked terpolymers of 2-methyl-2-[(1-oxo-2-propenyl)amino]-1-propanesulfonic acid partially salified in the form of the sodium salt, the potassium salt or the ammonium salt, of acrylamide and of N-isopropylacrylamide;

Crosslinked terpolymers of 2-methyl-2-[(1-oxo-2-propenyl)amino]-1-propanesulfonic acid partially salified in the form of the sodium salt, the potassium salt or the ammonium salt, of acrylamide and of N-[2-hydroxy-1,1-bis(hydroxymethyl)ethyl]propenamide;

crosslinked tetrapolymers of 2-methyl-2-[(1-oxo-2-propenyl)amino]-1-propanesulfonic acid partially salified in the form of the sodium salt, the potassium salt or the ammonium salt, of acrylic acid partially salified in the form of the sodium salt, the potassium salt or the ammonium salt, of acrylamide and of (2-hydroxyethyl)acrylate;

Crosslinked terpolymers of 2-methyl-2-[(1-oxo-2-propenyl)amino]-1-propanesulfonic acid partially salified in the form of the sodium salt, the potassium salt or the ammonium salt, of acrylamide and of (2-hydroxyethyl) acrylate.

According to another particular aspect of the present invention, the composition prepared by the process as hereinabove defined, comprises at least 50% by weight and not more than 70% by weight of polyelectrolyte. In this case, the composition is preferably prepared by performing the following process:

a) an aqueous phase containing the monomers and the possible hydrophilic additives is emulsified in an organic phase containing the surfactant system of water-in-oil (W/O) type, a mixture consisting of the oil intended to be present in the final composition and of a volatile oil, and the possible hydrophobic additives, b) The polymerization reaction is initiated by introducing a free-radical initiator into the emulsion formed in a), and the reaction is then allowed to proceed, and c) The reaction medium from step b) is concentrated by distillation until the said volatile oil has been completely removed.

The volatile oils that are suitable for performing the process as hereinabove defined are, for example, light isoparaffins containing from 8 to 11 carbon atoms, for instance those sold under the names Isopar™ G, Isopar™ L, Isopar™ H or Isopar™ J.

According to one preferred embodiment of the process as hereinabove defined, the polymerization reaction is initiated with a redox couple, such as the cumene hydroperoxide/sodium metabisulfite couple, at a temperature of less than or equal to 10° C., and is then performed either quasi-adiabatically up to a temperature of greater than or equal to 40° C. and more particularly greater than or equal to 50° C., or by controlling the change of the temperature.

When step c) is complete, the emulsifying system of oil-in-water type is introduced, if desired, at a temperature below 50° C.

When the composition as hereinabove defined comprises less than 50% by weight of polyelectrolyte, it is preferably prepared by performing the following process:

a) An aqueous phase containing the monomers and the possible additives is emulsified in an oil phase in the presence of one or more emulsifiers of water-in-oil type, b) The polymerization reaction is initiated by introducing a free-radical initiator into the emulsion formed in a), and the reaction is then allowed to proceed, c) When the polymerization reaction is complete, one or more emulsifiers of oil-in-water type are introduced, if desired, at a temperature below 50° C.

According to one variant of this process, the reaction medium obtained form step b) is concentrated by distillation before performing step c).

According to one preferred embodiment of the process as hereinabove defined, the polymerization reaction is initiated with a redox couple, such as the cumene hydroperoxide/sodium metabisulfite couple, at a temperature of less than or equal to 10° C., and is then performed either quasi-adiabatically up to a temperature of greater than or equal to 40° C. and more particularly greater than or equal to 50° C., or by controlling the change of the temperature.

According to another preferred embodiment of the process, the aqueous starting solution is adjusted to a pH of less than or equal to 4 before performing step a).

According to another particular aspect of the present invention, the composition as hereinabove defined comprises not more than 30% by weight of polyelectrolyte.

A subject of the invention is also a cosmetic, dermopharmaceutical or pharmaceutical composition, characterized in that it comprises as thickening and/or emulsifying compound at least one inverse latex obtained by the process, as hereinabove defined.

The cosmetic, dermocosmetic, dermopharmaceutical or pharmaceutical composition hereinabove defined generally comprises from 0.1% to 10% and more particularly between 0.5% and 5% by weight of the said inverse latex. It is especially in the form of a water-in-oil emulsion, an oil-in-water emulsion, a water-in-oil-in-water emulsion, an oil-in-water-in-oil emulsion, a milk, a lotion, a gel, a cream-gel, a cream, a soap, a bubble bath, a balm, a shampoo or a conditioner.

According to one preferred aspect of the present invention, the cosmetic, dermocosmetic, dermopharmaceutical or pharmaceutical composition as hereinabove defined is a topical composition.

A subject of the invention is also the use of the inverse latex obtained by the process, as hereinabove defined for preparing a cosmetic, dermopharmaceutical or pharmaceutical topical composition.

The topical composition according to the invention, intended to be applied to the skin or mucous membranes of man or animals, may consist of a topical emulsion comprising at least one aqueous phase and at least one oil phase. This topical emulsion may be of the oil-in-water type. More particularly, this topical emulsion may consist of a fluid emulsion, such as a milk or a fluid gel. The oil phase of the topical emulsion may consist of a mixture of one or more oils.

A topical composition according to the invention may be intended for cosmetic use or may be used to prepare a medicament for treating skin and mucous membrane diseases. In the latter case, the topical composition then comprises an active principle that may consist, for example, of an anti-inflammatory agent, a muscle relaxant, an anti-fungal agent or an antibacterial agent.

The compositions according to the invention may also contain ingredients usually used in the cosmetic and dermopharmaceutical fields and known to those skilled in the art, such as fats (oils, butters, waxes, fatty acids and gums), emulsifiers and coemulsifiers, gelling agents and/or stabilizers and/or film-forming agents, fillers, pigments, sunscreens, humectants, solvents and cosolvents, plasticizers, sequestrants, antioxidants, fragrances, preserving agents or active principles. As examples of oils that may be combined with the composition of the invention, mention may be made of paraffins, isoparaffins, white mineral oils, plant oils, animal oils, synthetic oils, silicone oils and fluoro oils; and more particularly:

oils of plant origin, such as sweet almond oil, coconut oil, castor oil, jojoba oil, olive oil, rapeseed oil, groundnut oil, sunflower oil, wheatgerm oil, corn germ oil, soybean oil, cottonseed oil, alfalfa oil, poppyseed oil, pumpkin oil, evening primrose oil, millet oil, barley oil, rye oil, safflower oil, candlenut oil, passionflower oil, hazelnut oil, palm oil, shea butter, apricot kernel oil, beauty-leaf oil, sysymbrium oil, avocado oil, calendula oil and floral or legume oils; ethoxylated plant oils; oils of animal origin, such as squalene and squalane; mineral oils, such as liquid paraffin, liquid petroleum jelly and isoparaffins; synthetic oils, especially fatty acid esters such as butyl myristate, propyl myristate, cetyl myristate, isopropyl palmitate, butyl stearate, hexadecyl stearate, isopropyl stearate, octyl stearate, isocetyl stearate, dodecyl oleate, hexyl laurate, propylene glycol dicaprylate, esters derived from lanolic acid, such as isopropyl lano late or isocetyl lano late, fatty acid monoglycerides, diglycerides and triglycerides, for instance glyceryl triheptanoate, alkylbenzoates, poly-α-olefins, polyolefins, for instance polyisobutene, synthetic isoalkanes, for instance isohexadecane, isododecane, perfluoro oils and silicone oils. Among the silicone oils, mention may be made more particularly of dimethylpolysiloxanes, methylphenylpolysiloxanes, silicones modified with amines, silicones modified with fatty acids, silicones modified with alcohols, silicones modified with alcohols and fatty acids, silicones modified with polyether groups, epoxy-modified silicones, silicones modified with fluoro groups, cyclic silicones and silicones modified with alkyl groups.

As another fatty substance that may be combined with the composition of the invention, mention may be made of fatty alcohols or fatty acids.

The fatty phase of the preparations according to the invention may also contain waxes such as beeswax; carnauba wax; candelilla wax, ouricury wax; japan wax; cork fibre wax or sugarcane wax; paraffin waxes; lignite waxes; microcrystalline waxes; lanolin wax; ozokerite; polyethylene wax; hydrogenated oils; silicone waxes; plant waxes; fatty alcohols and fatty acids that are solid at room temperature; glycerides that are solid at room temperature.

The inverse latex according to the invention may optionally be combined with other thickening and/or emulsifying polymers. Examples that may be mentioned include homopolymers or copolymers of acrylic acid or of acrylic acid derivatives, homopolymers or copolymers of acrylamide, homopolymers or copolymers of acrylamide derivatives, homopolymers or copolymers of acrylamidomethyl propanesulfonic acid, of vinyl monomer, of trimethylaminoethyl acrylate chloride sold under the names Carbopol™ Ultrez™ 10, Pemulen™ TR1, Pemulen™ TR2, Simulgel™ A, Simulgel™ NS, Simulgel™ EPG, Simulgel™ EG, Luvigel™ EM, Salcare™ SC91, Salcare™ SC92, Salcare™ SC95, Salcare™ SC96, Flocare™ ET100, Hispagel™, Sepigel™ 305, Sepigel™ 501, Sepigel™ 502, Sepiplus, Flocare™ ET58 and Stabileze™ 06; hydrocolloids of plant or biosynthetic origin, for instance xanthan gum, karaya gum, carrageenates or alginates; silicates; cellulose and its derivatives; starch and its hydrophilic derivatives; polyurethanes.

The composition according to the invention is also an advantageous substitute for those sold under the names Sepigel™ 305, Sepigel™ 501, Simulgel™ EG, Simulgel™ NS or Simulgel™ 600 by the Applicant, since it also shows good compatibility with the other excipients used for the preparation of formulations such as milks, lotions, creams, creamgels, soaps, bubblebaths, balms, shampoos or hair conditioners.

It is especially compatible with the concentrates described and claimed in the international publications WO 92/06778, WO 95/04592, WO 95/13863, WO 96/37285, WO 98/22207, and WO 98/47610 or in FR 2 734 496, with the surfactants described in WO 93/08204.

Among the emulsifiers that may be used in the presence of the inverse latex according to the invention, examples that may be mentioned include fatty acids; ethoxylated fatty acids; fatty acid esters of sorbitol; ethoxylated fatty acid esters; polysorbates; polyglycerol esters; ethoxylated fatty alcohols; sucrose esters; alkylpolyglycosides; sulfated or phosphated fatty alcohols or mixtures of alkylpolyglycosides and of fatty alcohols described in French patent applications 2 668 080, 2 734 496, 2 756 195, 2 762 317, 2 784 680, 2 784 904, 2 791 565, 2 790 977, 2 807 435 and 2 804 432, Sensanov and Fluidanov.

The cosmetic, dermocosmetic, dermopharmaceutical or pharmaceutical composition as hereinabove defined may also comprise texture agents and/or fillers, for instance acrylic and methacrylic acid copolymers, starches, silicas, calcium, magnesium, aluminium or barium silicates, calcium phosphate, natural fibres such as cotton fibre, cellulose fibre or chitosan fibre, or synthetic fibres such as polyamide (Nylon®) fibre, rayon fibre, viscose fibre, cellulose acetate fibre, poly-p-phenyleneterephthamide fibre (Kevlar®), polyethylene or polypropylene fibre, glass fibre, carbon fibre, Teflon fibre, polyester fibre, polyvinyl chloride fibre, polyvinyl alcohol fibre, polyacrylonitrile fibre, polyurethane fibre or polyethylene phthalate fibre, talc, mica, sericite, silica, boron nitride, lauroyllysine, silicone resin powders, calcium carbonate, magnesium carbonate, titanium oxide, zinc oxide or cerium oxide, titanium micas, iron oxides and other mineral or organic pigments, or a mixture of these powders.

As examples of active principles that may be combined with the inverse latex according to the invention, mention may be made of compounds with a lightening or depigmenting action, a moisturizing action, a tensioning action, a calmative or relaxing action, a purifying, seboregulatory or hair-loss-countering action, an anti-ageing action, or a firming, restructuring action, a free-radical-scavenging action, an antioxidant action or a self-tanning action. The composition of the invention may thus be combined with active agents such as, for example, arbutin, kojic acid, hydroquinone, ellagic acid, vitamin C and its derivatives, Stay C, magnesium ascorbyl phosphate and its derivatives, ascorbyl glucoside, phytic acid, fruit acids, lactic acid, rucinol or resorcinol, azeleic acid, glycolic acid, gluconic acid, dihydroxyacetone (DHA), erythrulose, lipoic acid, Vegewhite™, Gatuline™, Synerlight™, Biowhite™ Phytolight™, Dermalight™, Clariskin™, Melaslow™, Dermawhite™, Ethioline™, Melarest™, Gigawhite™, Albatine™, Lumiskin™, polyphenol extracts, grape extracts, pine extracts, wine extracts, olive extracts, tea extracts, cocoa extracts, Amazonian forest plant extracts, legume extracts, floral extracts, fruit extracts, mint extracts, pond extracts, N-acyl proteins, N-acyl peptides, for instance Matrixyl™, N-acylamino acids, partial hydrolysates of N-acyl proteins, amino acids, peptides, total protein hydrolysates, partial protein hydrolysates, polyols (for instance glycerol, butylene glycol, etc.), milk derivatives, Aquaxyl™, urea, pyrrolidonecarboxylic acid or derivatives of this acid, glycyrrhetinic acid or its derivatives, α-bisabolol, sugars or sugar derivatives, polysaccharides or derivatives thereof, hydroxy acids, for instance lactic acid or salicylic acid, vitamins, vitamin derivatives, for instance retinol, retinol derivatives, vitamin E and its derivatives, minerals, trace elements, extracts of rocks or stones, enzymes or derivatives thereof, coenzymes or derivatives thereof, for instance coenzyme Q10, hormones or "hormone-like" substances, for instance Phyto Age™, soybean extracts, for instance Raffermine™, wheat extracts, for instance Tensine™ or Gliadine™, plant extracts, tannin-rich plant extracts, isoflavonerich extracts or terpene-rich extracts, freshwater or saltwater algal extracts, marine extracts in general, including coral extracts, essential waxes, bacterial extracts, minerals, for instance the range of Givobio™ products and especially the calcium, magnesium, copper, cobalt, zinc, manganese, etc. derivatives, lipids in general, lipids such as ceramides or phospho lipids and also derivatives, active agents with a slimming action, for instance caffeine or its derivatives, active agents that improve the capillary circulation of the skin, for instance venotonic agents, draining active agents, decongestive active agents such as ginko biloba, ivy, common horsechestnut, bamboo, ruscus, centella asiatica, focus, rosemary or sage, active agents with antimicrobial activity or a purifying action on greasy skin, for instance copper or zinc derivatives or octopirox or Sensiva SC50, active agents with energizing or stimulating properties, for instance Sepitonic™, M3 or Physiogenyl™, panthenol and its derivatives, for instance Sepicap™ MP, anti-ageing active agents, Sepivinol™, Sepivital™, Manoliva™ and Phyto Age™. The composition of the invention may also more generally be combined with anti-ageing active agents for combating photoageing, the targeted active agents protecting the integrity of the dermo-epidermal junction, active agents that increase the synthesis of components of the extracellular matrix (for instance collagen, elastins, glycosaminoglycans, etc.), active agents that act favorably on chemical (cytokines) or physical (integrins) cell communication, active agents with a restructuring effect, active agents with a cicatrizing effect, active agents with a firming effect, active agents with a "botox-like" effect, active agents that act on expression wrinkles, active agents that act on the calcium channels, active agents that improve the integrity of the skin barrier, active agents that act on specific skin enzymes, active agents that act on specific cell receptors, active agents that improve cell communication, active agents with a free-radical-scavenging or antioxidant effect, active agents with a "tensioning" effect and active agents with an antidandruff, anti-acne, calmative or anti-neuromediator effect. The composition containing the polymer according to the invention may also be combined with active agents that afford a heating effect on the skin, such as skin capillary circulation activators (for example nicotinates) or ingredients that create, conversely, a sensation of freshness on application (for example menthol).

As sunscreens that may be incorporated with the composition of the invention, mention may be made of any of those featured in the amended Cosmetic Directive 76/768/EEC appendix VII.

According to this preferred aspect, the sunscreen is more particularly chosen from lipophilic sunscreens, for instance octocrylene, etocrylene, homosalate, for instance Eusolex™ HMS, octyl para-methoxycinnamate, for instance Parsol™ MCX, octinoxate, octisalate, avobenzone, oxybenzone, benzophenone-1, benzophenone-2, benzophenone-3, for instance Uvinul M-40, benzophenone-8, benzophenone-12, ethyl dihydroxypropyl PABA, glyceryl PABA, ethylhexyl dimethyl PABA, menthyl anthranilate, methylbenzylidenecamphor or isopropyl dibenzoyl methane.

The sunscreen as hereinabove defined may also comprise one or more lipophobic sunscreens, for instance titanium dioxide, zinc oxide, phenylbenzimidazolesulfonic acid, benzophenone-4, TEA salicylate, PABA and DEA methoxycinnamate.

The sunscreen as hereinabove defined may also comprise one or more oil absorbers, for instance silica, whether these are spherical silicas, for instance Spheron™ L-1500, porous silica or pyrogenic silica, crosslinked or non-crosslinked polymethyl methacrylate, for instance the Micropearl™ products, dextrins, cyclodextrins, molecular sieves, for instance zeolites, Nylon™ 6 or 12, sodium calcium aluminosilicate, talc or mica.

The sunscreen as hereinabove defined may also comprise one or more esters of neopentanoic acid with an isoalkyl alcohol containing from 10 to 22 carbon atoms. In this case, it preferably comprises isodecyl neopentanoate, isostearyl neopentanoate or isoarachidyl neopentanoate.

According to a particular aspect of the invention, the cosmetic, dermopharmaceutical or pharmaceutical composition comprises an efficient quantity of dihydroxyacetone and more particularly between 1% and 8% by weight of the composition of dihydroxyacetone.

According to a more particular aspect of the invention, the cosmetic, dermopharmaceutical or pharmaceutical composition comprises either dihydroxyacetone and at least a hydroxy acid such as lactic acid, salicylic acid, gluconic acid or kojic acid, either dihydroxyacetone and at least one sunscreen agent, either dihydroxyacetone and at least one moisturizing agent, either dihydroxyacetone and at least on slimming agent such as caffeine.

The examples that follow are intended to illustrate the present invention without, however, limiting it. They show that the novel inverse lattices do not irritate the skin and that their physical properties allow them to be used in the preparation of cosmetic, dermopharmaceutical or pharmaceutical compositions more particularly intended for treating sensitive skin.

EXAMPLE 1

Inverse Latex of (AMPS Na Salt)/AM Copolymer (40/60), Crosslinked With Methylenebis(Acrylamide), in Isopar M Prepared by the Process According to the Invention (Composition 1)

Preparation
   a)—The following are placed in a stirred reactor:
      246 g of 2-methyl-2-[(1-oxo-2-propenyl)amino]-1-propanesulfonic acid (in powder form)
      254 g of a commercial solution containing 50% acrylamide (AM) and
      0.45 g of sodium diethylenetriamine pentaacetate.
95.4 g of a 50% weight by weight of sodium hydroxide is then progressively poured into the reactor under stirring; in order to produce an aqueous solution with a pH of around 7; and 0.107 g of methylenebis(acrylamide) is then added.

The pH of this aqueous solution is adjusted to 6, with the addition of 0.4 g 2-methyl-2-[(1-oxo-2-propenyl)amino]-1-propanesulfonic acid (in powder form), and the aqueous phase weight is finally adjusted at 682 g by addition of water.
   b)—An organic phase is prepared by mixing together:
   220 g of Isopar™ M (C13-C14 isoparaffin),
   27.5 g of Witcamide™ 511 (partially esterified N,N-dialkanolamide),
   0.06 g of azobis(isobutyronitrile).
   c)—The aqueous phase is gradually introduced into the organic phase and the mixture is stirred vigorously using a Silverson™ or IKA™ stirrer, for example. The emulsion obtained is then transferred into a polymerization reactor, bled from air with nitrogen and then cooled to about 5-6° C. 10 g of a solution containing 0.5 g sodium persulfate is then added, followed, after homogenization of the solution, by addition of an aqueous solution of sodium metabisulfite (2.5% by weight in water) at a rate of 0.5 ml/minute for about 60 minutes, while allowing the temperature to rise at the end of polymerization. The reaction medium is then maintained for about 90 minutes at this temperature. Sodium metabisulfite is then added in order to obtain an acrylamide concentration in the final composition, less than 2 ppm. The reaction medium is then cooled and when the temperature of and the resulting compound reaches 25° C., 50 g Laureth™ 7 is added to obtain the expected inverse latex.

Evaluation of the Properties

Viscosity of the inverse latex at 2% by weight in de-ionized water (Brookfield RVT): η=82 800 mPa·s; pH=6.1

Viscosity of the inverse latex at 2% by weight in de-ionized water+0.1% NaCl (Brookfield RVT): r=30 200 mPa·s;

Preparation of an Aqueous Gel 98 g of deionized water are introduced into a 250 cm3 beaker and stirred at room temperature with mechanical stirrer equipped with an anchor modulus at 50 rpm. 2 g of the inverse latex as previously prepared, are progressively added into the stirred deionized water. The aqueous media thickens and a gel is formed. This gel is stirred at room temperature at 80 rpm in order to achieve a homogeneous appearance of such a gel.

The beaker containing the aqueous gel prepared as previously described is placed into a regulated oven at a temperature of 80° C. For each measurement of the acrylamide concentration, 5 g of the previously prepared gel, stored into the oven, are introduced into a 10 cm3 graduated flask at room temperature, with 1 g of sodium chloride under powder form. A saturated solution of sodium chloride is then added into the graduated flask in order to adjust the volume of the solution to 10 cm3. The graduated flask containing the diluted gel into the sodium chloride solution is manually stirred. Such a stirred solution of gel in sodium chloride is then filtered off and quantified by the mean of a High Performance Liquid Chromatograph equipped with a Ultra-Violet detector. After 24 h at 80° C. as well as after 48 h at 80° C., it is observed that the acrylamide concentration brought back to the starting inverse latex, stays under 2 ppm and does not increase along the time.

COMPARATIVE EXAMPLE 1

Inverse Latex of (AMPS Na Salt)/AM Copolymer (40/60), Crosslinked with Methylenebis(Acrylamide), Isopar M, Prepared by the Process According to State of the Art (Composition 2)

Preparation a) The following are placed in a stirred reactor:
496.3 g of a commercial aqueous solution containing 55% by weight 2-methyl-2-[(1-oxo-2-propenyl)amino]-1-propanesulfonic acid sodium salt,
127 g of acrylamide (AM),
0.45 g of sodium diethylenetriaminepentaacetate,
0.107 g of methylenebis(acrylamide).

The pH of this aqueous solution is adjusted to 6, with the addition of 0.4 g 2-methyl-2-[(1-oxo-2-propenyl)amino]-1-propanesulfonic acid (in powder form), and the aqueous phase weight is finally adjusted at 682 g by addition of water.

b)—An organic phase is prepared by mixing together:
220 g of Isopar™ M (C13-C14 isoparaffin),
27.5 g of Witcamide™ 511 (partially esterified N,N-dialkanolamide),
0.06 g of azobis(isobutyronitrile).

c)—The aqueous phase is gradually introduced into the organic phase and the mixture is stirred vigorously using a Silverson™ or IKA™ stirrer, for example. The emulsion obtained is then transferred into a polymerization reactor, bled from air with nitrogen and then cooled to about 5-6° C. 10 g of a solution containing 0.5 g sodium persulfate is then added, followed, after homogenization of the solution, by addition of an aqueous solution of sodium metabisulfite (2.5% by weight in water) at a rate of 0.5 cm3/minute for about 60 minutes, while allowing the temperature to rise at the end of polymerization. The reaction medium is then maintained for about 90 minutes at this temperature. Sodium metabisulfite is then added in order to obtain an acrylamide concentration in the final composition, less than 2 ppm. When the temperature of and the resulting compound reaches 25° C., 50 g Laureth™ 7 is added to obtain the expected inverse latex.

Evaluation of the Properties

Viscosity of the inverse latex at 2% by weight in de-ionized water (Brookfield RVT): η=99 000 mPa·s; pH=6.3

Viscosity of the inverse latex at 2% by weight in de-ionized water+0.1% NaCl (Brookfield RVT): η=30 000 mPa·s;

Preparation of an Aqueous Gel 98 g of deionized water are introduced into a 250 cm3 beaker and stirred at room temperature with mechanical stirrer equipped with an anchor modulus at 50 rpm. 2 g of the inverse latex as previously prepared, are progressively added into the stirred deionized water. The aqueous media thickens and a gel is formed. This gel is stirred at room temperature at 80 rpm in order to achieve a homogeneous appearance of such a gel.

The beaker containing the aqueous gel prepared as previously described is placed into a regulated oven at a temperature of 80° C. For each measurement of the acrylamide concentration, 5 g of the previously prepared gel, stored into the oven, are introduced into a 10 cm3 graduated flask at room temperature, with 1 g of sodium chloride under powder form. A saturated solution of sodium chloride is then added into the graduated flask in order to adjust the volume of the solution to 10 cm3. The graduated flask containing the diluted gel into the sodium chloride solution is manually stirred. Such a stirred solution of gel in sodium chloride is then filtered off and quantified by the mean of a High Performance Liquid Chromatograph equipped with a Ultra-Violet detector. After 24 h at 80° C. it is observed that the acrylamide concentration brought back to the starting inverse latex, increases until 60 ppm and after 48 h at 80° C., reaches 100 ppm.

It results therefrom, that the choice of the starting AMPS seems to be a key point in terms of acrylamide residue content. In fact and without being linked by the following considerations, the inventors believe that the presence of stabilizing compounds, which are present in AMPS aqueous solutions but not in AMPS powder, could have a strong influence on the potential existence of secondary reactions or on the polymerization itself that would affect the residual acrylamide rate and/or the stability of the inverse latex, after storage in inappropriate conditions of temperature and or light.

COMPARATIVE EXAMPLE 2

Inverse Latex of (AMPS Na Salt)/AM Copolymer (40/60), Crosslinked with Methylenebis(Acrylamide), Isohexadecane, Prepared by the Process According to State of the Art (Composition 3)

Preparation a) The following are placed into a stirred reactor:
80 g distilled water,
95.96 g of a 50% weight by weight aqueous sodium hydroxide solution,
246.7 g of [(1-oxo-2-propenyl)amino]-1-propanesulfonic acid is then progressively poured onto said sodium hydroxide media contained into said stirred reactor, followed by 253.8 g of a 50% weight by weight aqueous acrylamide solution and
0.45 g of sodium diethylenetriaminepentaacetate, and 0.132 g of methylenebis(acrylamide).

The pH of this aqueous solution is adjusted to 5, with the addition of 2-methyl-2-[(1-oxo-2-propenyl)amino]-1-propanesulfonic acid, and 682 g by addition of water.

b)—An organic phase is prepared by mixing together:
220 g of isohexadecane,
21 g of Witcamide™ 511 (partially esterified N,N-dialkanolamide),
0.06 g of azobis(isobutyronitrile).

c)—The aqueous phase is gradually introduced into the organic phase and the mixture is stirred vigorously using a Silverson™ or IKA™ stirrer, for example. The emulsion obtained is then transferred into a polymerization reactor, bled from air with nitrogen and then cooled to about 5-6° C. 10 g of a solution containing 0.5 g sodium persulfate is then added, followed, after homogenization of the solution, by addition of an aqueous solution of sodium metabisulfite (2.5% by weight in water) at a rate of 0.5 cm3/minute for about 60 minutes, while allowing the temperature to rise at the end of polymerization. The reaction medium is then maintained for about 90 minutes at this temperature. Sodium metabisulfite is then added in order to obtain an acrylamide concentration in the final composition, less than 2 ppm. When the temperature of and the resulting compound reaches 25° C., 50 g Laureth™ 7 is added to obtain the expected inverse latex.

Evaluation of the Properties

Viscosity of the inverse latex at 2% by weight in de-ionized water (Brookfield RVT): $\eta$=69 000 mPa·s;

Preparation of an Aqueous Gel 98 g of deionized water are introduced into a 250 cm$^3$ beaker and stirred at room temperature with mechanical stirrer equipped with an anchor modulus at 50 rpm. 2 g of the inverse latex as previously prepared, are progressively added into the stirred deionized water. The aqueous media thickens and a gel is formed. This gel is stirred at room temperature at 80 rpm in order to achieve a homogeneous appearance of such a gel.

The beaker containing the aqueous gel prepared as previously described is placed into a regulated oven at a temperature of 80° C. For each measurement of the acrylamide concentration, 5 g of the previously prepared gel, stored into the oven, are introduced into a 10 cm$^3$ graduated flask at room temperature, with 1 g of sodium chloride under powder form. A saturated solution of sodium chloride is then added into the graduated flask in order to adjust the volume of the solution to 10 cm$^3$. The graduated flask containing the diluted gel into the sodium chloride solution is manually stirred. Such a stirred solution of gel in sodium chloride is then filtered off and quantified by the mean of a High Performance Liquid Chromatograph equipped with a Ultra-Violet detector. After 24 h at 80° C. it is observed that the acrylamide concentration brought back to the starting inverse latex, increases until 60 ppm and after 48 h at 80° C., reaches 100 ppm.

It results there from, that without being limited by the theory, the inventors believe the reduction of the contact time between AMPS and soda has a positive effect which limits the risk AMPS degradation which could be a cause of the release of Acrylamide after along period of storage of the final cosmetic compositions The inventors also believe that the choice of the starting AMPS seems to be a key point in terms of acrylamide residue content because the presence of stabilizing compounds, which are present in AMPS aqueous solutions but not in AMPS powder, could also have a strong influence on the potential existence of secondary reactions or on the polymerization itself that would affect the residual acrylamide rate and/or the stability of the inverse latex, after storage in inappropriate conditions of temperature and or light.

EXAMPLES OF FORMULATIONS PREPARED WITH THE COMPOSITIONS ACCORDING TO THE INVENTION

EXAMPLE 2

Care Cream

| | |
|---|---|
| Cyclomethicone: | 10% |
| Inverse latex of Example 1: | 0.8% |
| Montanov ™ 68: | 2% |
| Stearyl alcohol: | 1.5% |
| Preserving agent: | 0.65% |
| Lysine: | 0.025% |
| EDTA (disodium salt): | 0.05% |
| Xanthan gum: | 0.2% |
| Glycerol: | 3% |
| Water: | qs 100% |

EXAMPLE 3

Aftershave Balm

| FORMULA | | |
|---|---|---|
| A | Inverse latex of Example 1: | 1.5% |
| | Water: | qs 100% |
| B | Micropearl ™ M 100: | 5.0% |
| | Sepicide ™ CI: | 0.50% |
| | Fragrance: | 0.20% |
| | 95° ethanol: | 10.0% |

Procedure
Add B to A.

EXAMPLE 4

Satin Body Emulsion

| FORMULA | | |
|---|---|---|
| A | Simulsol ™ 165: | 5.0% |
| | Lanol ™ 1688: | 8.50% |
| | Shea butter: | 2% |
| | Liquid paraffin: | 6.5% |
| | Lanol ™ 14M: | 3% |
| | Lanol ™ S: | 0.6% |
| B | Water: | 66.2% |
| C | Micropearl ™ M 100: | 5% |
| D | Inverse latex of Example 1: | 3% |
| E | Sepicide ™ CI: | 0.3% |
| | Sepicide ™ HB: | 0.5% |
| | Aquaxyl ™: | 3% |
| | Fragrance: | 0.20% |
| | Vitamin E acetate: | 0.20% |
| | Sodium pyrolidinonecarboxylate: | 1% |

Procedure

Add C to B, emulsify B in A at 70° C. and then add D at 60° C., followed by E at 30° C.

EXAMPLE 5

Oil-in-Water Cream

| | FORMULA | |
|---|---|---|
| A | Simulsol ™ 165: | 5.0% |
| | Lanol ™ 1688: | 20.0% |
| | Lanol ™ P: | 1.0% |
| B | Water: | qs 100% |
| C | Inverse latex of Example 1: | 2.50% |
| D | Sepicide ™ CI: | 0.20% |
| | Sepicide ™ HB: | 0.30% |

Procedure

Introduce B into A at about 75° C.; add C at about 60° C., then D at about 45° C.

EXAMPLE 6

Non-Greasy Antisun Gel

| | FORMULA | |
|---|---|---|
| A | Inverse latex of Example 1: | 3.00% |
| | Water: | 30% |
| B | Sepicide ™ CI: | 0.20% |
| | Sepicide ™ HB: | 0.30% |
| | Fragrance: | 0.10% |
| C | Dye: | qs |
| | Water: | 30% |
| D | Micropearl ™ M 100: | 3.00% |
| | Water: | qs 100% |
| E | Silicone oil: | 2.0% |
| | Parsol ™ MCX: | 5.00% |

Procedure

Introduce B into A; add C, then D, then E.

EXAMPLE 7

Antisun Milk

| | FORMULA | |
|---|---|---|
| A | Montanov ™ S: | 3.0% |
| | Sesame oil: | 5.0% |
| | Parsol ™ MCX: | 5.0% |
| | Carrageenan λ: | 0.10% |
| B | Water: | qs 100% |
| C | Inverse latex of Example 1: | 0.80% |
| D | Fragrance: | qs |
| | Preserving agent: | qs |

Procedure

Emulsify B in A at 75° C. then add C at about 60° C., followed by D at about 30° C., and adjust the pH if necessary.

EXAMPLE 8

Massage Gel

| | FORMULA | |
|---|---|---|
| A | Inverse latex of Example 1: | 3.5% |
| | Water: | 20.0% |
| B | Dye: | 2 drops/100 g |
| | Water: | qs |
| C | Alcohol: | 10% |
| | Menthol: | 0.10% |
| D | Silicone oil: | 5.0% |

Procedure

Add B to A, then add C to the mixture, followed by D.

EXAMPLE 9

Moisturizing and Matting Foundation

| | FORMULA | |
|---|---|---|
| A | Water: | 20.0% |
| | Butylene glycol: | 4.0% |
| | PEG-400: | 4.0% |
| | Pecosil ™ PS100: | 1.0% |
| | NaOH: | qs pH = 9 |
| | Titanium dioxide: | 7.0% |
| | Talc: | 2.0% |
| | Yellow iron oxide: | 0.8% |
| | Red iron oxide: | 0.3% |
| | Black iron oxide: | 0.05% |
| B | Lanol ™ 99: | 8% |
| | Caprylic/capric triglyceride: | 8% |
| | Montanov ™ 202: | 5.00% |
| C | Water: | qs 100% |
| | Micropearl ™ M305: | 2.0% |
| | Tetrasodium EDTA: | 0.05% |
| D | Cyclomethicone: | 4.0% |
| | Xanthan gum: | 0.2% |
| | Inverse latex of Example 1: | 0.8% |
| E | Sepicide ™ HB: | 0.5% |
| | Sepicide ™ CI: | 0.3% |
| | Fragrance: | 0.2% |

Procedure

Prepare mixtures B+D and A+C at 80° C., then mix together and emulsify the whole.

EXAMPLE 10

Radiance Gel

| | FORMULA | |
|---|---|---|
| A | Inverse latex of Example 1: | 4% |
| | Water: | 30% |
| B | Elastine HPM: | 5.0% |
| C | Micropearl ™ M 100: | 3% |
| | Water: | 5% |
| D | Sepicide ™ CI: | 0.2% |

EXAMPLE 11

Body Milk

| FORMULA | |
|---|---|
| Montanov ™ S: | 3.5% |
| Lanol ™ 37T: | 8.0% |
| Solagum ™ L: | 0.05% |
| Water: | qs 100% |
| Benzophenone-3: | 2.0% |
| Dimethicone 350 cPs: | 0.05% |
| Inverse latex of Example 1: | 0.8% |
| Preserving agent: | 0.2% |
| Fragrance: | 0.4% |

Continued formula:
Sepicide ™ HB: 0.3%
Fragrance: 0.06%
Sodium pyrolidinonecarboxylate 50%: 1%
Water: qs 100%

Procedure
Prepare A; add B, then C, then D.

EXAMPLE 12

Makeup-Removing Emulsion with Sweet Almond Oil

| FORMULA | |
|---|---|
| Montanov ™ 68: | 5% |
| Sweet almond oil: | 5% |
| Water: | qs 100% |
| Inverse latex of Example 1: | 0.3% |
| Glycerol: | 5% |
| Preserving agent: | 0.2% |
| Fragrance: | 0.3% |

EXAMPLE 13

Moisturizing Cream for Greasy Skin

| FORMULA | |
|---|---|
| Montanov ™ 68: | 5% |
| Cetylstearyl octanoate: | 8% |
| Octyl palmitate: | 2% |
| Water: | qs 100% |
| Inverse latex of Example 1: | 0.6% |
| Micropearl ™ M 100: | 3.0% |
| Mucopolysaccharides: | 5% |
| Sepicide ™ HB: | 0.8% |
| Fragrance: | 0.3% |

EXAMPLE 14

Alcohol-Free Soothing Aftershave Balm

| | FORMULA | |
|---|---|---|
| A | Lipacide ™ PVB: | 1.0% |
| | Lanol ™ 99: | 2.0% |
| | Sweet almond oil: | 0.5% |
| B | Inverse latex of Example 1: | 3.5% |
| C | Water: | qs 100% |
| D | Fragrance: | 0.4% |
| | Sepicide ™ HB: | 0.4% |
| | Sepicide ™ CI: | 0.2% |

EXAMPLE 15

Cream with AHA for Sensitive Skin

| FORMULA | |
|---|---|
| Mixture of lauryl amino acids: | 0.1% to 5% |
| Magnesium potassium aspartate: | 0.002% to 0.5% |
| Lanol ™ 99: | 2% |
| Montanov ™ 68: | 5.0% |
| Water: | qs 100% |
| Inverse latex of Example 1: | 1.50% |
| Gluconic acid: | 1.50% |
| Triethylamine: | 0.9% |
| Sepicide ™ HB: | 0.3% |
| Sepicide ™ CI: | 0.2% |
| Fragrance: | 0.4% |

EXAMPLE 16

After-Sun Soothing Care

| FORMULA | |
|---|---|
| Mixture of lauryl amino acids: | 0.1% to 5% |
| Magnesium potassium aspartate: | 0.002% to 0.5% |
| Lanol ™ 99: | 10.0% |
| Water: | qs 100% |
| Inverse latex of Example 1: | 2.50% |
| Sepicide ™ HB: | 0.3% |
| Sepicide ™ CI: | 0.2% |
| Fragrance: | 0.4% |
| Dye: | 0.03% |

EXAMPLE 17

Makeup-Removing Milk

| FORMULA | |
|---|---|
| Sepiperl ™ N: | 3% |
| Primol ™ 352: | 8.0% |
| Sweet almond oil: | 2% |

-continued

| FORMULA | |
|---|---|
| Water: | qs 100% |
| Inverse latex of Example 1: | 0.8% |
| Preserving agent: | 0.2% |

EXAMPLE 18

Fluid Foundation

| FORMULA | |
|---|---|
| Simulsol ™ 165: | 5.0% |
| Lanol ™ 84D: | 8.0% |
| Lanol ™ 99: | 5.0% |
| Water: | qs 100% |
| Mineral fillers and pigments: | 10.0% |
| Inverse latex of Example 1: | 1.2% |
| Preserving agent: | 0.2% |
| Fragrance: | 0.4% |

EXAMPLE 19

Antisun Milk

| FORMULA | |
|---|---|
| Sepiperl ™ N: | 3.5% |
| Lanol ™ 37T: | 10.0% |
| Parsol ™ MCX: | 5.0% |
| Eusolex ™ 4360: | 2.0% |
| Water: | qs 100% |
| Inverse latex of Example 1: | 1.8% |
| Preserving agent: | 0.2% |
| Fragrance: | 0.4% |

EXAMPLE 20

Eye Contour Gel

| FORMULA | |
|---|---|
| Inverse latex of Example 1: | 2.0% |
| Fragrance: | 0.06% |
| Sodium pyrrolidinonecarboxylate: | 0.2% |
| Dow Corning ™ 245 Fluid: | 2.0% |
| Water: | qs 100% |

EXAMPLE 21

Leave-in Care Composition

| FORMULA | |
|---|---|
| Inverse latex of Example 1: | 1.5% |
| Fragrance: | qs |
| Preserving agent: | qs |
| Dow Corning ™ X2 8360: | 5.0% |
| Dow Corning ™ Q2 1401: | 15.0% |
| Water: | qs 100% |

EXAMPLE 22

Slimming Gel

| FORMULA | |
|---|---|
| Inverse latex of Example 1: | 5% |
| Ethanol: | 30% |
| Menthol: | 0.1% |
| Caffeine: | 2.5% |
| Extract of ruscus: | 2% |
| Extract of ivy: | 2% |
| Sepicide ™ HB: | 1% |
| Water: | qs 100% |

EXAMPLE 23

Ultra-Natural Tinted Cream-Gel

| | FORMULA | |
|---|---|---|
| A | Water: | 10.0% |
| | Butylene glycol: | 4.0% |
| | PEG-400: | 4.0% |
| | Pecosil ™ PS100: | 1.5% |
| | NaOH: | qs pH = 7 |
| | Titanium dioxide: | 2.0% |
| | Yellow iron oxide: | 0.8% |
| | Red iron oxide: | 0.3% |
| | Black iron oxide: | 0.05% |
| B | Lanol ™ 99: | 4.0% |
| | Caprylic/capric triglyceride: | 4.0% |
| | Sepifeel ™ One: | 1.0% |
| | Inverse latex of Example 1: | 3.0% |
| C | Water: | qs 100% |
| | Micropearl ™ M305: | 2.0% |
| | Tetrasodium EDTA: | 0.05% |
| | Cyclomethicone: | 4.0% |
| D | Sepicide ™ HB: | 0.5% |
| | Sepicide ™ CI: | 0.3% |
| | Fragrance: | 0.2% |

Procedure

Prepare the mixture B+C, then add A and then D.

EXAMPLE 24

Care for Greasy Skin

| | FORMULA | |
|---|---|---|
| A | Micropearl ™ M310: | 1.0% |
| | Inverse latex of Example 1: | 5.0% |
| | Octyl isononanoate: | 4.0% |
| B | Water: | qs 100% |
| C | Sepicontrol ™ A5: | 4.0% |
| | Fragrance: | 0.1% |
| | Sepicide ™ HB: | 0.3% |
| | Sepicide ™ CI: | 0.2% |
| D | Capigel ™ 98: | 0.5% |
| | Water: | 10% |

EXAMPLE 25

Cream with AHA

| | FORMULA | |
|---|---|---|
| A | Montanov ™ 68: | 5.0% |
| | Lipacide ™ PVB: | 1.05% |
| | Lanol ™ 99: | 10.0% |
| B | Water: | qs 100% |
| | Gluconic acid: | 1.5% |
| | TEA (triethanolamine): | 0.9% |
| C | Inverse latex of Example 1: | 1.5% |
| D | Fragrance: | 0.4% |
| | Sepicide ™ HB: | 0.2% |
| | Sepicide ™ CI: | 0.4% |

EXAMPLE 26

Non-Greasy Self-Tanning Product for the Face and Body

| | FORMULA | |
|---|---|---|
| A | Lanol ™ 2681: | 3.0% |
| | Inverse latex of Example 1: | 2.5% |
| B | Water: | qs 100% |
| | Dihydroxyacetone: | 3.0% |
| C | Fragrance: | 0.2% |
| | Sepicide ™ HB: | 0.8% |
| | NaOH (sodium hydroxide): | qs pH = 5 |

EXAMPLE 27

Antisun Milk with Monoï de Tahiti

| | FORMULA | |
|---|---|---|
| A | Monoi de Tahiti: | 10% |
| | Lipacide ™ PVB: | 0.5% |
| | Inverse latex of Example 1: | 2.2% |

| | FORMULA | |
|---|---|---|
| B | Water: | qs 100% |
| C | Fragrance: | 0.1% |
| | Sepicide ™ HB: | 0.3% |
| | Sepicide ™ CI: | 0.1% |
| | Parsol ™ MCX: | 4.0% |

EXAMPLE 28

Antisun Care Product for the Face

| | FORMULA | |
|---|---|---|
| A | Cyclomethicone and dimethiconol: | 4.0% |
| | Inverse latex of Example 1: | 3.5% |
| B | Water: | qs 100% |
| C | Fragrance: | 0.1% |
| | Sepicide ™ HB: | 0.3% |
| | Sepicide ™ CI: | 0.21% |
| | Parsol ™ MCX: | 5.0% |
| | Titanium mica: | 2.0% |
| | Lactic acid: | qs pH = 6.5 |

EXAMPLE 29

Self-Tanning Emulsion

| | FORMULA | |
|---|---|---|
| A | Lanol ™ 99: | 15% |
| | Montanov ™ 68: | 5.0% |
| | Parsol ™ MCX: | 3.0% |
| B | Water: | qs 100% |
| | Dihydroxyacetone: | 5.0% |
| | Monosodium phosphate: | 0.2% |
| C | Inverse latex of Example 1: | 0.5% |
| D | Fragrance: | 0.3% |
| | Sepicide ™ HB: | 0.8% |
| | NaOH: | qs pH = 5 |

EXAMPLE 30

Care Cream

| | |
|---|---|
| Cyclomethicone: | 10% |
| Inverse latex of Example 1: | 0.8% |
| Montanov ™ 68: | 4.5% |
| Preserving agent: | 0.65% |
| Lysine: | 0.025% |
| EDTA (disodium salt): | 0.05% |
| Xanthan gum: | 0.2% |
| Glycerol: | 3% |
| Water: | qs 100% |

EXAMPLE 31

Care Cream

| | |
|---|---|
| Cyclomethicone: | 10% |
| Inverse latex of Example 1: | 0.8% |
| Montanov ™ 68: | 4.5% |
| Perfluoropolymethyl isopropyl ether: | 0.5% |
| Preserving agent: | 0.65% |
| Lysine: | 0.025% |
| EDTA (disodium salt): | 0.05% |
| Pemulen ™ TR1: | 0.2% |
| Glycerol: | 3% |
| Water: | qs 100% |

EXAMPLE 32

Body Milk

| | FORMULA | |
|---|---|---|
| A | Simulsol ™ 165: | 5.0% |
| | Lanol ™ 1688: | 12.0% |
| | Lanol ™ 14 M: | 2.0% |
| | Cetyl alcohol: | 0.3% |
| | Schercemol ™ OP: | 3% |
| B | Water: | qs 100% |
| C | Inverse latex of Example 1: | 0.35% |
| D | Sepicide ™ CI: | 0.2% |
| | Sepicide ™ HB: | 0.5% |
| | Fragrance: | 0.20% |

Procedure

Emulsify B in A at about 75° C.; add C at about 60° C., followed by D at about 30° C.

EXAMPLE 33

Massage Care Gel

| | FORMULA | |
|---|---|---|
| A | Inverse latex of Example 1: | 3.00% |
| | Water: | 30% |
| B | Sepicide ™ CI: | 0.20% |
| | Sepicide ™ HB: | 0.30% |
| | Fragrance: | 0.05% |
| C | Dye: | qs |
| | Water: | qs 100% |
| D | Micropearl ™ SQL: | 5.0% |
| | Lanol ™ 1688: | 2% |

Procedure
Prepare A; add B, then C and then D.

EXAMPLE 34

Body Milk

| | FORMULA | |
|---|---|---|
| A | Sepiperl ™ N: | 3.0% |
| | Glyceryl triheptonate: | 10.0% |
| B | Water: | qs 100% |
| C | Inverse latex of Example 1: | 1.0% |
| D | Fragrance: | qs |
| | Preserving agent: | qs |

Procedure

Melt A at about 75° C. Emulsify B in A at 75° C. then add C at about 60° C., followed by D.

EXAMPLE 35

Alcohol-Free Soothing Aftershave Balm

| FORMULA | |
|---|---|
| Mixture of lauryl amino acids: | 0.1% to 5% |
| Magnesium potassium aspartate: | 0.002% to 0.5% |
| Lanol ™ 99: | 2% |
| Sweet almond oil: | 0.5% |
| Water: | qs 100% |
| Inverse latex of Example 1: | 3% |
| Sepicide ™ HB: | 0.3% |
| Sepicide ™ CI: | 0.2% |
| Fragrance: | 0.4% |

EXAMPLE 36

Body Milk

| FORMULA | |
|---|---|
| Sepiperl ™ N: | 3.5% |
| Lanol ™ 37T: | 8.0% |
| Solagum ™ L: | 0.05% |
| Water: | qs 100% |
| Benzophenone-3: | 2.0% |
| Dimethicone 350 cPs: | 0.05% |
| Inverse latex of Example 1: | 0.8% |
| Preserving agent: | 0.2% |
| Fragrance: | 0.4% |

EXAMPLE 37

Alcohol-Free Soothing Aftershave Balm

| | FORMULA | |
|---|---|---|
| A | Lipacide ™ PVB: | 1.0% |
| | Lanol ™ 99: | 2.0% |
| | Sweet almond oil: | 0.5% |

EXAMPLE 37 (continued)

FORMULA

| | | |
|---|---|---|
| B | Inverse latex of Example 1: | 3.5% |
| C | Water: | qs 100% |
| D | Fragrance: | 0.4% |
| | Sepicide ™ HB: | 0.4% |
| | Sepicide ™ CI: | 0.2% |

EXAMPLE 38

Refreshing Aftershave Gel

FORMULA

| | | |
|---|---|---|
| A | Lipacide ™ PVB: | 0.5% |
| | Lanol ™ 99: | 5.0% |
| | Inverse latex of Example 1: | 2.5% |
| B | Water: | qs 100% |
| C | Micropearl ™ LM: | 0.5% |
| | Fragrance: | 0.2% |
| | Sepicide ™ HB: | 0.3% |
| | Sepicide ™ CI: | 0.2% |

EXAMPLE 39

Cream with AHAs

FORMULA

| | | |
|---|---|---|
| A | Montanov ™ 68: | 5.0% |
| | Lipacide ™ PVB: | 1.05% |
| | Lanol ™ 99: | 10.0% |
| B | Water: | qs 100% |
| | Gluconic acid: | 1.5% |
| | TEA (triethanolamine): | 0.9% |
| C | Inverse latex of Example 1: | 1.5% |
| D | Fragrance: | 0.4% |
| | Sepicide ™ HB: | 0.2% |
| | Sepicide ™ CI: | 0.4% |

EXAMPLE 40

Gloss Gel

| | |
|---|---|
| Inverse latex of Example 1: | 1.5% |
| Volatile silicone: | 25% |
| Monopropylene glycol: | 25% |
| Demineralized water: | 10% |
| Glycerol: | qs 100% |

EXAMPLE 41

Slimming Gel

| | |
|---|---|
| Inverse latex of Example 1: | 1.5% |
| Isononyl isononanoate: | 2% |
| Caffeine: | 5% |
| Ethanol: | 40% |
| Micropearl ™ LM: | 2% |
| Demineralized water: | qs 100% |
| Preserving agent, fragrance: | qs |

EXAMPLE 42

Makeup-Removing Milk

| | |
|---|---|
| Simulsol ™ 165: | 4% |
| Montanov ™ 202: | 1% |
| Caprylate/caprate triglyceride: | 15% |
| Pecosil ™ DCT: | 1% |
| Demineralized water: | qs |
| Capigel ™ 98: | 0.5% |
| Inverse latex of Example 1: | 1% |
| Proteol ™ APL: | 2% |
| Sodium hydroxide: | qs pH = 7 |

EXAMPLE 43

Restructuring "Rinse-Off" Cream Mask for Stressed and Embrittled Hair

FORMULA

| | |
|---|---|
| Ketrol ™ T: | 0.5% |
| Pecosil ™ SPP50: | 0.75% |
| N-Cocoyl amino acids: | 0.70% |
| Butylene glycol: | 3.0% |
| Inverse latex of Example 1: | 3.0% |
| Montanov ™ 82: | 3.0% |
| Jojoba oil: | 1.0% |
| Lanol ™ P: | 6.0% |
| Amonyl ™ DM: | 1.0% |
| Lanol ™ 99: | 5.0% |
| Sepicide ™ HB: | 0.3% |
| Sepicide ™ CI: | 0.2% |
| Fragrance: | 0.2% |
| Water: | qs 100% |

EXAMPLE 44

Antisun Cream

| | |
|---|---|
| Simulsol ™ 165: | 3% |
| Montanov ™ 202: | 2% |
| C12-C15 benzoate: | 8% |
| Pecosil ™ PS 100: | 2% |
| Dimethicone: | 2% |
| Cyclomethicone: | 5% |

-continued

| | |
|---|---|
| Octyl para-methoxycinnamate: | 6% |
| Benzophenone-3: | 4% |
| Titanium oxide: | 8% |
| Xanthan gum: | 0.2% |
| Butylene glycol: | 5% |
| Demineralized water: | qs 100% |
| Inverse latex of Example 1: | 1.5% |
| Preserving agent, fragrance: | qs |

EXAMPLE 45

Care Gel for Combination Skin

| | |
|---|---|
| Inverse latex of Example 1: | 4% |
| Plant squalane: | 5% |
| Dimethicone: | 1.5% |
| Sepicontrol ™ A5: | 4% |
| Xanthan gum: | 0.3% |
| Water: | qs 100% |
| Preserving agent, fragrance: | qs |

EXAMPLE 46

Hair Lotion

| FORMULA | |
|---|---|
| Butylene glycol: | 3.0% |
| Inverse latex of Example 1: | 3% |
| Simulsol ™ 1293: | 3.0% |
| Lactic acid: | qs pH = 6 |
| Sepicide ™ HB: | 0.2% |
| Sepicide ™ CI: | 0.3% |
| Fragrance: | 0.3% |
| Water: | qs 100% |

EXAMPLE 47

Protective and Relaxing Shampoo

| FORMULA | |
|---|---|
| Amonyl ™ 675 SB: | 5.0% |
| 28% sodium lauryl ether sulfate: | 35.0% |
| Inverse latex of Example 1: | 3.0% |
| Sepicide ™ HB: | 0.5% |
| Sepicide ™ CI: | 0.3% |
| Sodium hydroxide: | qs pH = 7.2 |
| Fragrance: | 0.3% |
| Dye (FDC Blue 1/Yellow 5): | qs |
| Water: | qs 100% |

EXAMPLE 48

"Leave-on" Protective Product Anti-Stress Haircare

| FORMULA | |
|---|---|
| Ketrol ™ T: | 0.5% |
| Mixture of cocoyl amino acids: | 3.0% |
| Butylene glycol: | 5.0% |
| DC 1501: | 5.0% |
| Composition of Example 1: | 4.0% |
| Sepicide ™ HB: | 0.5% |
| Sepicide ™ CI: | 0.3% |
| Fragrance: | 0.3% |
| Water: | qs 100% |

EXAMPLE 49

Cream with Vitamins

| | |
|---|---|
| Simulsol ™ 165: | 5% |
| Montanov ™ 202: | 1% |
| Caprylic/capric triglycerides: | 20% |
| Vitamin A palmitate: | 0.2% |
| Vitamin E acetate: | 1% |
| Micropearl ™ M305: | 1.5% |
| Inverse latex of Example 1: | 2% |
| Water: | qs 100% |
| Preserving agent, fragrance: | qs |

EXAMPLE 50

Antisun Gel

| FORMULA | |
|---|---|
| Inverse latex of Example 1: | 3.00% |
| Sepicide ™ CI: | 0.20% |
| Sepicide ™ HB: | 0.30% |
| Fragrance: | 0.10% |
| Dye: | qs |
| Silica: | 3.00% |
| Water: | qs 100% |
| Silicone oil: | 2.0% |
| Benzophenone-3: | 5.00% |

EXAMPLE 51

Lip Gloss

| FORMULA | |
|---|---|
| Inverse latex of Example 1: | 1.50% |
| Schercemol ™ TISC: | 15.00% |
| Vistanol ™ NPGC: | 15.00% |
| Candurin Paprika: | 0.50% |
| Montanox ™ 80: | 1.00% |
| Antaron ™ V216: | 0.90% |

-continued

| FORMULA | |
| --- | --- |
| Apricot flavouring: | 0.20% |
| Sepicide ™ HB: | 0.50% |
| C Maltidex ™ H16322: | qs 100% |

EXAMPLE 52

Pressed Powder for Sunny Climate

| FORMULA | |
| --- | --- |
| Inverse latex of Example 1: | 2.00% |
| Lanol ™ 99: | 12.00% |
| Sepiwhite ™ MSH: | 1.00% |
| Talc: | 33.00% |
| Micropearl ™ M310: | 3.00% |
| Yellow iron oxide: | 0.80% |
| Red iron oxide: | 0.30% |
| Black iron oxide: | 0.05% |
| Mica: | qs 100% |

EXAMPLE 53

Emulsion for Atopic Skin

| FORMULA | |
| --- | --- |
| Arlacel ™ P135: | 2.00% |
| Inverse latex of Example 1: | 1.00% |
| Lanol ™ 1688: | 14.00% |
| Primol ™ 352: | 8.00% |
| Glycerol: | 5.00% |
| Water: | qs 100% |
| Magnesium sulfate: | 0.70% |
| Sepicide ™ HB: | 0.30% |
| Sepicide ™ CI: | 0.20% |
| Micropearl ™ M310: | 5.00% |

EXAMPLE 54

Soothing Antisun Care (Water-in-Silicone)

| FORMULA | |
| --- | --- |
| Inverse latex of Example 1: | 2.00% |
| DC5225C: | 20.00% |
| DC345: | 10.00% |
| Sepicalm ™ VG: | 3.00% |
| Titanium dioxide MT100T: | 5.00% |
| Zinc oxide Z-Cote HP1: | 5.00% |
| Sepicide ™ HB: | 0.30% |
| Fragrance: | 0.05% |
| Sepicide ™ CI: | 0.20% |
| Glycerol: | 5.00% |
| Sodium chloride: | 2.00% |
| Water: | qs 100% |

EXAMPLE 55

Multi-Phase Care

| FORMULA | |
| --- | --- |
| Inverse latex of Example 1: | 3.00% |
| C12-15 alkylbenzoate: | 25.00% |
| Aquaxyl ™: | 3.00% |
| Sepitonic ™ M3: | 1.00% |
| Sepicide ™ HB: | 0.50% |
| Sepicide ™ CI: | 0.30% |
| Water: | qs 100% |

EXAMPLE 56

Self-Tanning Gel

| | |
| --- | --- |
| Inverse latex of Example 1: | 5% |
| Ethanol: | 30% |
| Dihydroxyacetone | 4% |
| Erythrulose | 1% |
| Menthol: | 0.1% |
| Caffeine: | 2.5% |
| Extract of ivy: | 2% |
| Sepicide ™ HB: | 1% |
| Water: | qs 100% |

EXAMPLE 57

Self-Tanning Antisun Milk

| FORMULA | | |
| --- | --- | --- |
| A | Sepiperl ™ N: | 3.0% |
| | Glyceryl triheptonate: | 10.0% |
| | Lipacide ™ PVB: | 0.5% |
| | Inverse latex of Example 1: | 2.2% |
| B | Water: | qs 100% |
| | Dihydroxyacetone | 5.0% |
| C | Fragrance: | 0.1% |
| | Sepicide ™ HB: | 0.3% |
| | Sepicide ™ CI: | 0.1% |
| | Parsol ™ MCX: | 4.0% |

EXAMPLE 58

Self-Tanning Cream with AHAs

| FORMULA | | |
| --- | --- | --- |
| A | Montanov ™ 68: | 5.0% |
| | Lipacide ™ PVB: | 1.05% |
| | Lanol ™ 99: | 10.0% |
| B | Water: | qs 100% |
| | Gluconic acid: | 1.5% |
| | dihydroxyacetone | 3.0% |
| | TEA (triethanolamine): | 0.9% |

-continued

| FORMULA | | |
|---|---|---|
| C | Inverse latex of Example 1: | 1.5% |
| D | Fragrance: | 0.4% |
|   | Sepicide ™ HB: | 0.2% |
|   | Sepicide ™ CI: | 0.4% |

EXAMPLE 59

Self-Tanning Cream with AHA for Sensitive Skin

| FORMULA | |
|---|---|
| Mixture of lauryl amino acids: | 0.1% to 5% |
| Magnesium potassium aspartate: | 0.002% to 0.5% |
| Lanol ™ 99: | 2% |
| Montanov ™ 68: | 5.0% |
| Water: | qs 100% |
| Inverse latex of Example 1: | 1.50% |
| Lactic acid: | 1.50% |
| Dihydroxyacetone | 3.5% |
| Triethylamine: | 0.9% |
| Sepicide ™ HB: | 0.3% |
| Sepicide ™ CI: | 0.2% |
| Fragrance: | 0.4% |

EXAMPLE 60

Satin Self-Tanning Moisturizing Emulsion

| FORMULA | | |
|---|---|---|
| A | Simulsol ™ 165: | 5.0% |
|   | Lanol ™ 1688: | 8.50% |
|   | Shea butter: | 2% |
|   | Liquid paraffin: | 6.5% |
|   | Lanol ™ 14M: | 3% |
|   | Lanol ™ S: | 0.6% |
| B | Water: | 66.2% |
|   | Dihydroxyacetone | 3% |
| C | Micropearl ™ M 100: | 5% |
| D | Inverse latex of Example 1: | 3% |
| E | Sepicide ™ CI: | 0.3% |
|   | Sepicide ™ HB: | 0.5% |
|   | Aquaxyl ™: | 5% |
|   | Fragrance: | 0.20% |
|   | Vitamin E acetate: | 0.20% |
|   | Sodium pyrolidinonecarboxylate: | 1% |

The definitions of the commercial products used in the examples are as follows:
Simulsol™ 1293 is hydrogenated and ethoxylated castor oil, with an ethoxylation index equal to 40, sold by the company SEPPIC.
Capigel™ 98 is a liquid thickener based on acrylate copolymer sold by the company SEPPIC.
Ketrol™ T is xanthan gum sold by the company Kelco.
Lanol™ 99 is isononyl isononanoate sold by the company SEPPIC.
DC1501 is a mixture of cyclopentasiloxane and dimethiconol sold by the company Dow Chemical.
Montanov™ 82 is an emulsifier based on cetearyl alcohol and cocoylglucoside.
Montanov™ 68 (cetearyl glucoside) is a self-emulsifying composition as described in WO 92/06778, sold by the company SEPPIC.
Micropearl™ M 100 is an ultra-fine powder with a very soft feel and a matting action, sold by the company Matsumo.
Sepicide™ CI, imidazolidineurea, is a preserving agent sold by the company SEPPIC.
Pemulen™ TR1 is an acrylic polymer sold by Goodrich.
Simulsol™ 165 is self-emulsifying glyceryl stearate sold by the company SEPPIC.
Lanol™ 1688 is an emollient ester with a non-greasy effect sold by the company SEPPIC.
Lanol™ 14M and Lanol® S are consistency factors sold by the company SEPPIC.
Sepicide™ HB, which is a mixture of phenoxyethanol, methylparaben, ethylparaben, propylparaben and butylparaben, is a preserving agent sold by the company SEPPIC.
Aquaxyl™ is a moisturizer sold by the company SEPPIC.
Schercemol™ OP is an emollient ester with a non-greasy effect.
Lanol™ P is an additive with a stabilizing effect sold by the company SEPPIC.
Parsol™ MCX is octyl para-methoxycinnamate; sold by the company Givaudan.
Sepiperl™ N is a nacreous agent, sold by the company SEPPIC, based on a mixture of alkylpolyglucosides such as those described in WO 95/13863.
Micropearl™ SQL is a mixture of microparticles containing squalane, which is released by the action of massaging; it is sold by the company Matsumo.
Lanol™ 99 is isononyl isononanoate sold by the company SEPPIC.
Lanol™ 37T is glyceryl triheptanoate, sold by the company SEPPIC.
Solagum™ L is a carrageenan sold by the company SEPPIC.
Marcol™ 82 is a liquid paraffin sold by the company Exxon.
Lanol™ 84D is dioctyl malate sold by the company SEPPIC.
Parsol NOX™ is a sunscreen sold by the company Givaudan.
Eusolex™ 4360 is a sunscreen sold by the company Merck.
Dow Corning™ 245 Fluid is cyclomethicone, sold by the company Dow Corning.
Lipacide™ PVB is an acylated wheat protein hydrolysate sold by the company SEPPIC.
Micropearl™ LM is a mixture of squalane, polymethyl methacrylate and menthol, sold by the company SEPPIC.
Sepicontrol™ A5 is a mixture of capryloylglycine, sarcosine and extract of Cinnamon zylanicum, sold by the company SEPPIC, such as those described in international patent application PCT/FR98/01313 filed on 23 Jun. 1998.
Lanol™ 2681 is a coconut caprylate/caprate mixture sold by the company SEPPIC.
Montanov™ 202 is an APG/fatty alcohol composition as described in WO 98/47610, sold by the company SEPPIC.
Proteol™ APL is a foaming surfactant sold by the company SEPPIC.
Schercemol™ TISC is an ester (triisostearyl citrate) sold by the company Scher.
Vistanol™ NPGC is an ester (neopentyl glycol dicaprate) sold by the company Sewa Kasei.
Antaron™ V216 is a synthetic polymer (PVP/hexadecene copolymer) distributed by the company Univar.
C Maltidex™ H16322 is a polyol (maltitol syrup) sold by the company Cerestar.
Sepiwhite™ MSH is a depigmenting active agent (undecylenoyl phenylalanine) sold by the company SEPPIC.
DC 345 is a cyclomethicone sold by the company Dow Corning.

DC 5225C is a mixture of cyclopentasiloxane and dimethiconecopolyol sold by the company Dow Corning.

Sepicalm™ VG is a soothing active agent (sodium palmitoylproline) sold by the company SEPPIC.

MT100VT is a micronized titanium dioxide that has undergone a surface treatment (aluminium hydroxide/stearic acid) distributed by the company Unipex.

Z-Cote HP 1 is a micronized zinc oxide that has undergone a surface treatment, distributed by Gattefosse.

Candurin Paprika is a mixture of potassium aluminium silicate and iron oxide.

The invention claimed is:

1. A process for the preparation of a composition comprising an oil phase, an aqueous phase, at least one emulsifying system of water-in-oil (W/O) type in the form of an inverse latex comprising from 20% to 70% by weight of a branched or crosslinked polyelectrolyte, wherein the said polyelectrolyte is a copolymer of 2-acrylamido-2-methylpropanesulfonic acid partially or totally salified with acrylamide, said preparation process being an inversed emulsion polymerization process wherein the polymerization of the monomers is conducted in a water-in oil emulsion, said process comprising:
    mixing a powder of 2-methyl-2-[(1-oxo-2-propenyl)amino]-1-propanesulfonic in acid form with an aqueous solution of acrylamide to form an aqueous solution;
    progressively neutralizing said aqueous solution by an aqueous alkalinized solution to form a neutralized aqueous solution; and
    adjusting the pH of said neutralized solution to about 6 with additional powder of 2-methyl-2-[(1-oxo-2-propenyl)amino]-1-propanesulfonic in acid form and water to form the aqueous phase, which is involved in the subsequent inversed emulsion polymerization by weight;
    wherein the polyelectrolyte comprises between 60 mol % and 20 mol % of partially or totally salified 2-methyl-2-[(1-oxo-2-propenyl)amino]-1-propanesulfonic acid monomer and between 40 mol % and 80 mol % of acrylamide monomer.

2. The process for the preparation of a composition as defined in claim 1, wherein the polyelectrolyte comprises between 50 mol % and 30 mol % of partially or totally salified 2-methyl-2-[(1-oxo-2-propenyl)amino]-1-propanesulfonic acid monomer and between 50 mol % and 70 mol % of acrylamide monomer.

3. The process for the preparation of a composition as defined in claim 1, wherein the composition comprises an emulsifying system of oil-in-water (O/W) type.

4. The process for the preparation of a composition as defined in claim 1, wherein the polyelectrolyte is selected from the group consisting of:
    crosslinked copolymers of 2-methyl-2-[(1-oxo-2-propenyl)amino]-1-propanesulfonic acid partially salified in the form of the sodium salt and of acrylamide;
    crosslinked copolymers of 2-methyl-2-[(1-oxo-2-propenyl)amino]-1-propanesulfonic acid partially salified in the form of the ammonium salt and of acrylamide; and
    crosslinked copolymers of 2-methyl-2-[(1-oxo-2-propenyl)amino]-1-propanesulfonic acid partially salified in the form of the potassium salt and of acrylamide.

5. The process for the preparation of a composition as defined in claim 1, wherein the composition is in the form of an inverse latex comprising from 25% to 50% by weight of the branched or crosslinked polyelectrolyte.

6. The process for the preparation of a composition as defined in claim 1, wherein the composition comprises at least one emulsifying system of oil-in-water (0/W) type.

7. The process for the preparation of a composition as defined in claim 1, wherein a chelating agent is mixed with the powder of 2-methyl-2-[(1-oxo-2-propenyl)amino]-1-propanesulfonic in acid form and the aqueous solution of acrylamide to form the aqueous solution.

8. The process for the preparation of a composition as defined in claim 1, wherein a chelating agent and a crosslinking agent are mixed with the powder of 2-methyl-2-[(1-oxo-2-propenyl)amino]-1-propanesulfonic in acid form and the aqueous solution of acrylamide to form the aqueous solution.

9. The process for the preparation of a composition as defined in claim 1, wherein a crosslinking agent is mixed with the powder of 2-methyl-2-[(1-oxo-2-propenyl)amino]-1-propanesulfonic in acid form and the aqueous solution of acrylamide to form the aqueous solution.

10. The process for the preparation of a composition as defined in claim 1, further comprising adding a crosslinking agent to said neutralized aqueous solution before adjusting the pH of said neutralized aqueous solution.

* * * * *

UNITED STATES PATENT AND TRADEMARK OFFICE
CERTIFICATE OF CORRECTION

PATENT NO. : 8,512,684 B2  Page 1 of 1
APPLICATION NO. : 12/738150
DATED : August 20, 2013
INVENTOR(S) : Mallo et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 285 days.

Signed and Sealed this
Fifteenth Day of September, 2015

Michelle K. Lee
*Director of the United States Patent and Trademark Office*